United States Patent [19]
Yazdanian et al.

[11] Patent Number: 6,093,553
[45] Date of Patent: Jul. 25, 2000

[54] IMMORTALIZED BRAIN ENDOTHELIAL CELLS

[75] Inventors: Mehran Yazdanian, Danbury; Barbara J. Bormann, Southington, both of Conn.

[73] Assignee: Boehringer Ingelheim Pharmaceuticals, Inc., Ridgefield, Conn.

[21] Appl. No.: 09/200,063

[22] Filed: Nov. 25, 1998

[51] Int. Cl.[7] .............................. C12Q 1/08; C12Q 1/68; C07H 21/04; C12P 21/06; C12N 5/00

[52] U.S. Cl. .................................. 435/40.51; 536/23.72; 435/6; 435/69.1; 435/325

[58] Field of Search ...................... 536/23.72; 435/69.1, 435/325, 6, 40.51

[56] References Cited

U.S. PATENT DOCUMENTS

| | | | |
|---|---|---|---|
| 5,674,722 | 10/1997 | Mulligan et al. | 435/172.3 |
| 5,733,761 | 3/1998 | Treco et al. | 435/172.3 |

FOREIGN PATENT DOCUMENTS

| | | |
|---|---|---|
| WO 89/05345 | 6/1989 | WIPO . |
| WO 93/06222 | 4/1993 | WIPO . |
| WO 96/11278 | 4/1996 | WIPO . |

OTHER PUBLICATIONS

Durieu–Trautmann, O., Immortalization of Brain Capillary Endothelial Cells with Maintenance of Structural Characteristics of the Blood–Brain Barrier Endothelium, In Vitro Cell Dev. Biol., Oct. 1991 pp. 771–777.

DeBault, Lawrence E., Cerebral Microvessels and Derived Cells in Tissue Culture: Establishment, Identification and Preliminary Characterization of an Endothelial Cell Line, In Vitro vol.k 17, No. 6, Jun. 1981, pp. 480–494.

Vicart, Patrick, Immortalization of Multiple Cell Types from Transgenic Mice Using a Transgene Containing the Vimentin Promoter and a Conditional Oncogene, Experimental Cell Research 214, pp. 35–45.

Roux, F. Regulation of Gamma–Glutamyl Transpeptidase and Alkaline Phosphatase Activities in Immortalized Rat Brain Microvessel Endothelial Cells, Journal of Cellular Physiology 159:101–113 (1994).

Aguzzi, Adriano, Cell type–specific tumor induction in neural transplants by retrovirus–mediated oncogene transfer, Oncogene (1991),6, 113–118.

Treisman, R., Transformation of rat cells by an altered polyoma virus genome expressing only the middle–T protein, Nature vol. 292, Aug. 13, 1981, pp. 595–600.

Soeda, Eiichi; Coding potential and regulatory signals of the polyoma virus genome, Nature vol. 283, Jan. 31, 1980, 445—453.

Juillerat–Jeanneret, L.; Dexamethasone Selectively Regulates the Activity of Enzymatic Markers of Cerebral Endothelial Cell Lines; In Vitro Cel Dev. Bio.—Jul.–Aug. 1992, pp. 537–543.

*Primary Examiner*—Hankyel Park
*Attorney, Agent, or Firm*—Robert P. Raymond; Anthony P. Bottino; Alan R. Stempel

[57] ABSTRACT

A brain microvessel endothelial cell having a Middle-T antigen gene from papovirus is disclosed. The brain microvessel endothelial cell exhibits normal cell phenotype, maintains the phenotype in culture and forms monolayers substantially impermeable to low molecular weight molecules. The cells are useful for in vitro studies involving the blood brain barrier. Also disclosed, are methods of using and processes of making these cells.

7 Claims, 3 Drawing Sheets

IMMORTALIZED BRAIN ENDOTHELIAL CELLS

TECHNICAL FIELD OF INVENTION

The invention relates to immortalized cellular clones of brain microvessel endothelial cells produced by transfection with a plasmid containing the middle-T antigen gene from polyoma virus. The cells described herein display and maintain an endothelial cell phenotype and spontaneously form confluent monolayers substantially impermeable to small molecules. The cells are therefore useful for in vitro models studying the blood brain barrier.

BACKGROUND OF THE INVENTION

The blood brain barrier (BBB) is composed of brain microvessel endothelial cells (referred to hereafter as BMECs) and acts as a regulatory interface for permeability of drugs and solutes between the blood and central nervous system (CNS). Isolation and culture of BMECs have led to the development of in vitro model systems for studying the BBB (Bowman et. al, 1983, Audus and Borchardt, 1986).

In vitro BBB model systems have been successfully derived from bovine, canine, human, murine, porcine, and rat brains and were found to have similar permeability properties due to similarity of the physiological characteristics of the BBB among all mammals (Cserr et al, 1984, Audus et al, 1990). In these models, BMECs retain the characteristics of brain endothelial cells in vivo including morphology, specific BBB enzyme markers, and tight intercellular junctions which can be useful for studying a variety of CNS drug delivery issues ranging from passive diffusion, carrier mediated transport, and metabolism to specific factors affecting the BBB permeability. However, passaging of BMECs results in loss of specific endothelial and BBB markers as well as tight intercellular junctions (Brightman and Neuwelt, 1989).

Presently, only primary cultures of BMECs have been developed to address the BBB permeability issues in vitro. Isolated and cultured primary brain cells developed previously have exhibited different properties primarily due to considerable variety in the starting material. For example, with respect to transcellular transport, rigorous comparison of data between different laboratories has been very difficult (Pardridge et al., 1990, Masereeuw et al., 1994). Passaging primary cells can affect the differentiation of cells and lead to the selection of the most rapidly proliferating clones. Furthermore, the expression of some marker enzymes such as gamma-glutmayl transpeptidase as well as tight junctional complexity has been shown to decrease with time in culture and passage number (Méresse et. al., 1989).

Papoviruses such as SV-40 and polyoma virus are known to produce tumors in rodents. The polyoma virus DNA sequence has been determined and the 'early region' which includes the small, middle and large T antigens has been indicated to be responsible for tumor formation. See Soeda et al., 1980, incorporated herein by reference. Previous methods using the SV 40 large T antigen gene disclose immortalization of bovine brain capillary endothelial cells in which the cells retain the differentiated phenotype and appear morphologically normal (Durieu-Trautmann et al., 1991). Fetal rat stems cells transfected with the middle T antigen gene produced two cell lines of endothelial cells that were not oncogenic, however, these cell lines do not spontaneously form a barrier to small hydrophilic molecules (Juillerat-Jeanneret et al., 1992).

Thus, it is apparent that the presently available clones of immortalized BMEC cultures suffer from individual drawbacks in terms of phenotype expression and homogeneic maintenance of that expression. This leads to difficulties with respect to accuracy and reproducibility in studies utilizing BMECs.

SUMMARY OF THE INVENTION

All of the above factors provide a strong incentive for the development of immortalized BMECs capable of maintaining a differentiated phenotype in culture and therefore, measurements such as permeability can be made without the need for repeated isolations of BMECs. The BMECs of the present invention provide a convenient, ready-to-use bank of cells as an efficient alternative to the use primary BMECs.

It is therefore an object of the invention to provide immortalized BMECs possessing a nucleic acid sequence encoding the middle-T antigen gene from a papovirus, such cells are capable of forming monolayers substantially impermeable to low molecular weight molecules. In preferred embodiments, there are provided BMECs having the middle-T antigen gene from the polyoma papovirus.

It is a further object of the present invention to provide a method of using the BMECs described herein for measuring permeability via passive diffusion or active transport, carrier mediated transport, efflux transport system such as P-glycoprotein and multi-drug resistance associated proteins (MRP), and metabolism of substances crossing the blood brain barrier such as pharmaceuticals.

It is yet a further object of the present invention to provide a process of making the immortalized BMECs described herein by providing primary culture BMECs, subsequently transfecting them with a vector containing the middle-T antigen gene from a papovirus, incubating the vectors and cells and subsequently isolating the immortalized BMECs possessing the middle-T antigen nucleic acid sequence.

These and other objectives will be readily appreciated by those of ordinary skill in the art based upon the following detailed disclosure of this invention.

BRIEF DESCRIPTION OF THE DRAWINGS

FIG. 2: FIG. 2 shows morphological comparisons of BMEC (A) and TBMEC, p11 (B)by light microscopy (200×).

DETAILED DESCRIPTION OF THE INVENTION

The subject cell line referred to herein as TBMEC,P11 has the A.T.C.C. designation number CRL-12414 having been deposited on Oct. 7, 1997, at the ATCC, Rockville, Md. U.S.A.

The present invention relates to immortalized BMECs, preferably mammalian BMECs, more preferably bovine BMECs, processes of making and methods of using these cells. For the first time, the present invention provides BMECs with the capability of preserving a fully differentiated phenotype and thus, the endothelial nature of these cells. This is accomplished by transfecting the BMECs with a vector such as a plasmid, containing the entire coding region of middle-T antigen gene from papoviruses such as polyoma or SV40. In preferred embodiments, there are provided a plasmid which carries the nucleic acid sequence encoding Middle T antigen from polyoma virus, such plasmid referred to herein as polyoma middle T (pyMT). Clones of the transfected cells are characterized in that they express and retain their differentiated phenotype. The BMECs according to the present invention grow as monolayers and show substantial impermeability to small substances imparted by their ability to form confluent monolayers. The aforementioned substances include low molecular weight hydrophilic and lipophilic pharmaceuticals and other chemicals. Examples of these low molecular weight molecules include:

acetylsalicylic acid, acyclovir, aminopyrine, caffeine, chlorpromazine, cimetidine, clonidine, corticosterone, desipramine, diazepam, dopamine, estradiol, hydrocortisone, indomethacin, mannitol, methyl scopolamine, nicotine, phenytoin, pirenzepine, progesterone, propranolol, salicylic acid, scopolamine, sucrose, sulfasalazine, terbutaline, testosterone, uracil, dexamethasone, urea, warfarin, bremazocine, meloxicam, nevirapine, ranitidine, didanosine, zalcitabine, stavudine and Saquinavir.

The term "differentiated phenotype" as used in the present invention shall be understood to mean BMECs forming continuous monolayers of oblong contact inhibited cells.

The term "substantially impermeable" as used in the present invention shall be understood to mean having low permeability coefficients similar to that of sucrose, a non-metabolizable paracellular marker.

Immortalized BMECs produced by transfection with a plasmid containing the middle-T antigen gene from polyoma virus displayed a non-transformed endothelial cell phenotype, i.e., they stained for phenotypical genetic markers such as Factor VIII and LDL receptor, and retained tight junction formation and permeability characteristics.

Cell morphology of one of the BMEC clones according to the present invention, TBMEC,P11 and BMEC cultures was examined with a microscope using phase contrast optics. TBMEC,P11 cells form continuous non-overlapping tightly packed monolayers of contact inhibited oblong cells with similar morphology to the primary BMECs when grown on collagen-coated and fibronectin treated petri dishes. With respect to studying maintenance of differentiated endothelial phenotype, the TBMEC,P11 was grown as monolayers in Transwell® plates and the permeability of sucrose, a non-metabolizable paracellular marker, was measured in primary BMECs and the TBMEC,P11 and was shown to be comparable. The permeability coefficient values for acyclovir and leucine were also shown to be comparable at similar concentrations. See Example 4.

It is therefore also an object of the present invention to provide a method of measuring blood brain barrier permeability of a substance by providing BMECs according to the invention in one or more confluent monolayers, contacting the substance with said confluent monolayer(s); and measuring the amount of said substance permeated across the BMEC monolayer(s). The method can measure passive diffusion or active transport and in addition can be varied, as appreciated by those skilled in the art, to perform characteristic measurements such as carrier mediated transport wherein permeability values as described in Example 3 are measured as a function of concentration of the solute or in the presence of ATP inhibitors such as sodium azide. Efflux transport can be measured wherein measuring permeability values as described in Example 3 is performed in the presence of inhibitors of the efflux pumps such as, but not limited to, cyclosporin-A, dexamethasone, digoxin, FK506, methadone, phenytoin, prazosin, quinidine, rhodamine 123, tamoxifen, verapamil, and yohimibine as well as all those listed by Seelig 1997, incorporated herein by reference. The methods of the present invention can also be used to measure blood brain barrier metabolism of a substance by measuring permeability values as described in Example 3 and profiling the metabolic degradation of compounds of interest as a function of time using quantitative analytical techniques such as high pressure liquid chromatography and mass spectrometry.

Immortalized BMECs provided by the present invention can be prepared by the following general method:

Primary cultures of BMECs can be prepared according to known methods. One example is bovine brain endothelium prepared from fresh calf brains as described previously (Audus and Borchardt, 1986). Briefly, three to four freshly excised bovine brains were purchased from a local slaughter house and transported to the laboratory in ice cold MEM. The capillaries and meninges were removed from each brain and the gray matter was scraped off and minced. The gray matter suspension was treated with protease and collagenase/dispase to separate the endothelial cells from the fat, myelin, and other cells. Microvessel endothelial cells were collected from a Percoll gradient, washed with MEM, and pelleted. They were then resuspended in a culture medium made of approximate equal parts MEM and F-12 Ham nutrient mix containing about 20% horse serum and about 5% DMSO and frozen under liquid nitrogen for 0–12 months, preferably not more then six months.

Figure 2A:
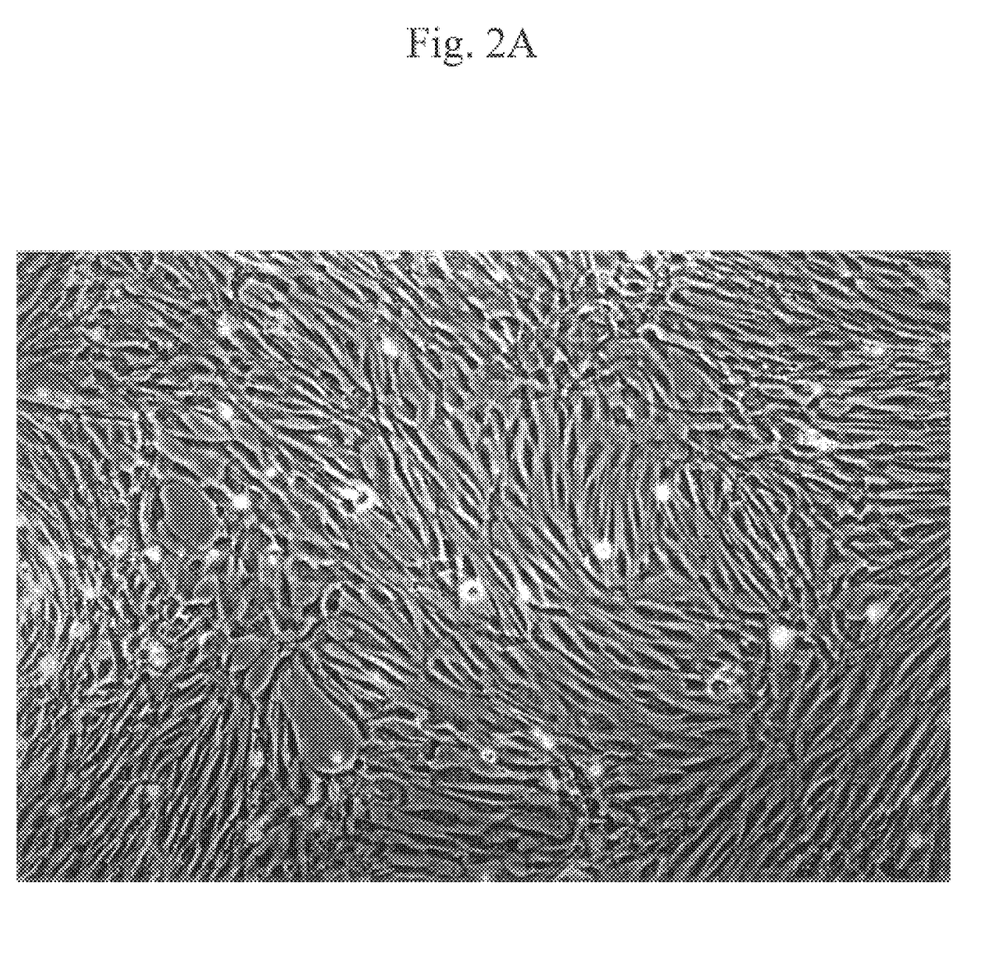
Figure 2B:
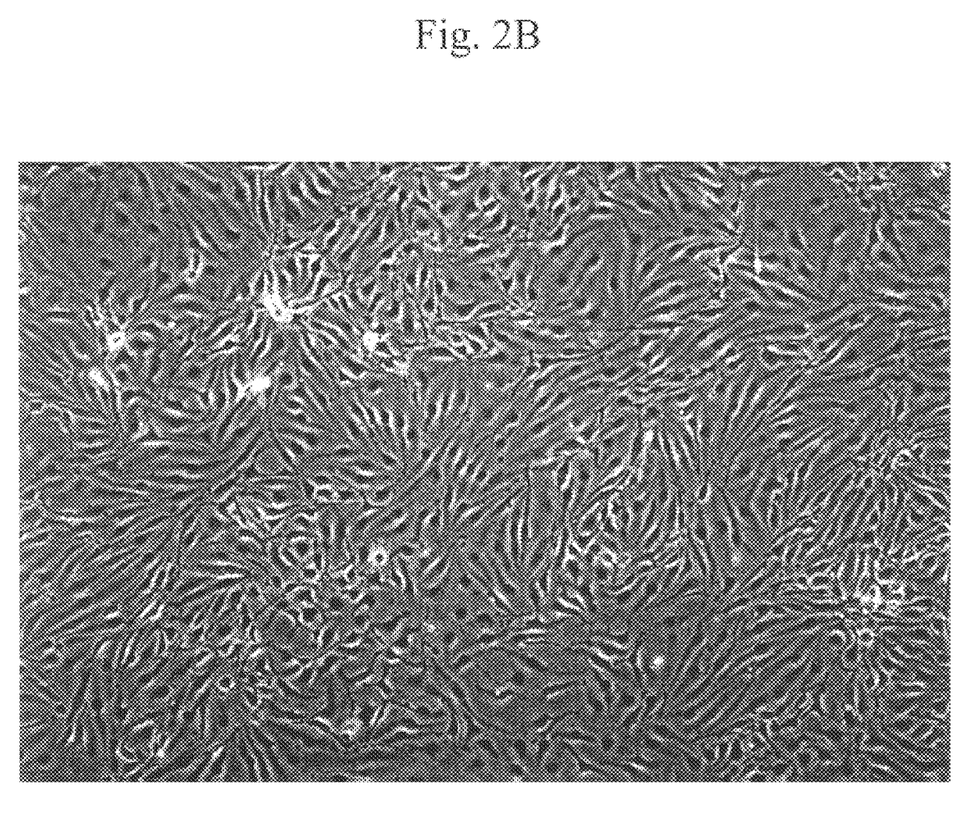

The BMECs above are then transfected as follows: The BMECs are transfected with a plasmid containing the middle-T antigen gene from polyoma virus. The plasmid pyMT (see example 5) carries the entire coding region of the Middle T antigen from polyoma virus {Soeda et al., 1980). Here, both the pSV2 neo plasmid, which carries the neo gene (Southern and Berg) for resistance to the aminoglycoside G418, and the pyMT plasmid were cotransfected into a primary stock of BMECs at about 50% confluency. About 20 $\mu$g of each vector was used in a calcium phosphate transfection procedure. Plasmids were allowed to incubate with the cells for about 30 minutes at room temperature and then incubated in complete culture medium for about 2.5 hours at about 37° C. The complete culture medium was made up of equal parts MEM and F-12 Ham nutrient mix containing amphotericin B (2.5 $\mu$/mL), ECGS (15 $\mu$g/mL), HEPES (10 mM), horse serum (10%), penicillin (100 Units/mL), polymoxin B (50 $\mu$g/mL), and streptomycin (100 $\mu$g/mL). After about 3 hours the cells were subjected to a DMSO (10%) osmotic shock for about 10 minutes. The cells are then washed, preferably about 7 times, with complete culture medium and returned to the incubator. Cells were split 1:1 into complete culture medium supplemented with G418 (300 $\mu$g/ml, activity) after they reached confluency (about 48 hours). Selective medium was changed about every 2 to 3 days. Foci appeared within 10 days. The foci were trypsinized, pooled and cultured through several passages. All clones had normal phenotypes but more regular and faster dividing time than the original primary BMECs (FIG. 2B). One of these clones, named TBMEC,P11 was further characterized and used in permeability experiments.

In order that this invention be more fully understood, the following examples are set forth. These examples are for the purpose of illustrating preferred embodiments of this invention, and are not to be construed as limiting the scope of the invention in any way.

EXAMPLE 1

Detection of pyMT Gene in TBMEC,P11

The presence of PyMT gene in TBMEC,P11 cells was determined by polymerase chain reaction (PCR). Genomic DNA was extracted from non-transfected (WT) and transfected (TX) BMEC and used at 10 ng/ml for PCR amplification. PyMT plasmid DNA was used as a positive control. The primers used for PCR amplification were as follows and were based on the published sequence (Soeda et.al, 1980).
230(S)-5'CCCAGACAACTATGGGGGGAT 3'
281(S)-5'CAGTCACTGCTACTGCACCCA 3'
971(S)-5'GCAACCCGACCTATTCTGTTA 3'
660(AS)-5'CGGGTTGGTGTTCCAAACCAT 3'
1030(AS)-5'GTTGGAGAACTCGGGTTGGGG 3'
1150(AS)-5'CCAGCTGGTCTTGGTCGCTTT 3'
PCR reactions were set up using 45 μl PCR Supermix (Gibco BRL), 2.5 μl each of the sense (S) and antisense (AS) primers (20 uM stock) and 10 ul of template DNA (10 ng/ml). Thirty cycles of PCR amplification was performed by melting DNA at 95° C. for 1 min, annealing at 50° C. for 1 min and extending at 72° C. for 1 min for each cycle using GeneAmp PCR System 9600 (Perkin Elmer). After 30 cycles, the final extension was performed for 7 mins at 72° C. and the products were resolved using 1.0% agarose gels.

Figure 1:
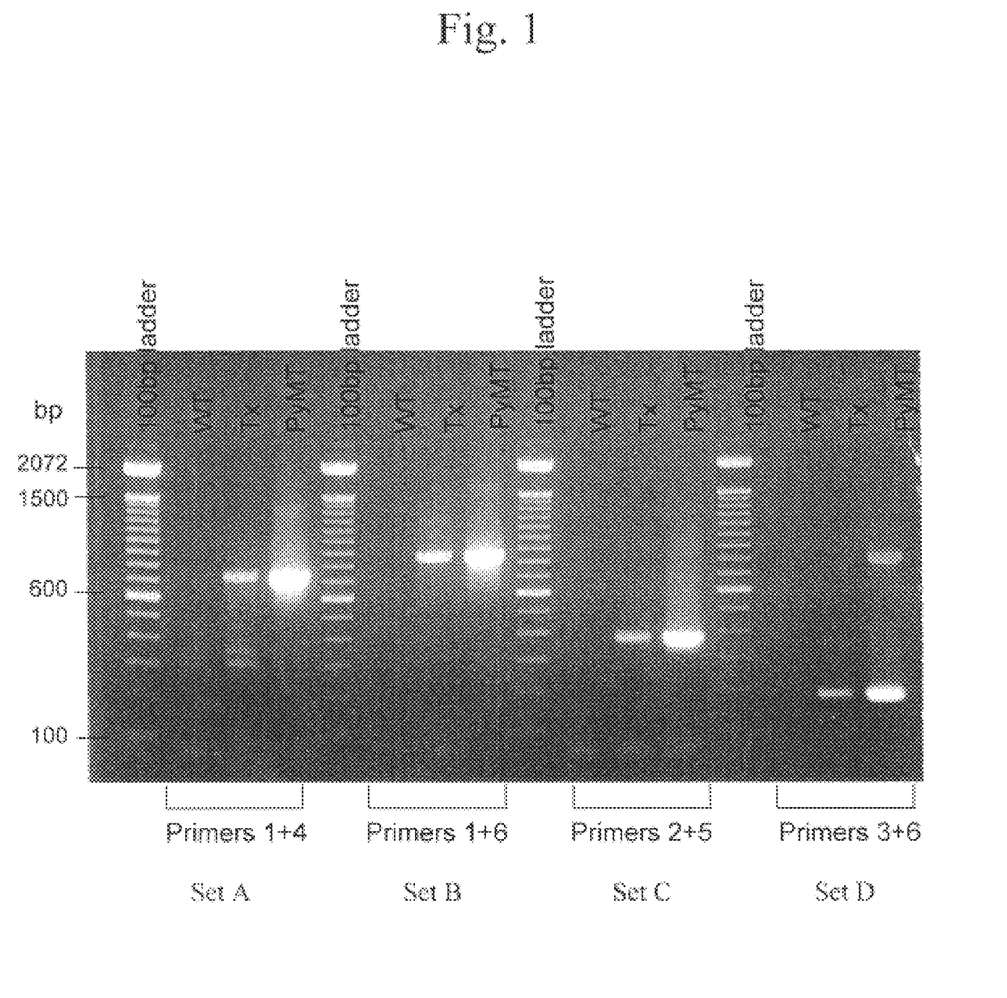
FIG. 1: shows results of the PCR amplification performed various primers from the polyoma middle-T antigen coding region.

Detection of transfected pyMT gene encoding Middle T Antigen:

Since TBMEC,P11 cells were co-transfected with a target DNA (pyMT) and a plasmid containing a selectable marker (pSV2neo), and then selected for G418 antibiotic resistance, it was preferable to detect pyMT gene in G418-resistant clones. Results of the PCR amplification performed using various primers from the polyoma middle T antigen coding region are shown in FIG. 1. Set A represents amplification using primers 230(S) and 1030(AS) generating a PCR product of 701 bp, set B using primers 230(S) and 1150(AS) for a product of 821 bp, set C using primers 281(S) and 660(AS) for a product of 380 bp and set D represents amplification using primers 971(S) and 1150(AS) giving rise to a PCR product of 180 bp. PCR amplification was detected only in the reactions where PyMT plasmid DNA and genomic DNA from transfected cells were used as templates. Template DNA from non-transfected BMEC cells did not show PCR amplification. These results confirm the presence of PyMT gene in TBMEC,P11 cells selected for G418 resistance.

EXAMPLE 2

Histochemical Techniques

Low density lipoprotein (LDL) uptake and Factor VIII antigen and gamma-glutamyl transpeptidase expression, specific markers found only in endothelial cells, were examined by immunohistochemical techniques. Cells were grown to near confluence on non-autofluorescent 25 mm plastic dishes. Uptake of acetylated low density lipoprotein labelled with 1,1'=dioctadecyl-3,3,3',3'-tetramethylinocabocyanine perchlorate (DiI-Ac-LDL) at 10 μg/ml in PBS was performed for 4 h at 37° C. The cells were examined by fluorescence microscopy. Negative controls used 50% rabbit serum in HBSS as a substitute for the primary antibody. BMECs grown in culture were also shown to stain histochemically positive for alkaline phosphatase, an enzyme marker for brain endothelial cells.

EXAMPLE 3

Permeability Experiments

BMEC and TBMEC,P11 cells were seeded at densities of 75,000 and 60,000 cells/mL respectively, onto polycarbonate filters in Transwell®, 6-well plates (Costar Transwell® 12 mm diameter, 0.4 μm pore size, Corning Costar Corp., Cambridge, Mass.) and were cultured in complete culture medium. The plates were maintained in an incubator at 37° C. and 5% $CO_2$ and were used for permeability experiments within 10 to 12 days postseeding for BMEC cells and 4 to 6 days postseeding for TBMEC,P11 cells.

Drug solutions were prepared in HBSS. All drug solutions also contained 0.1 mM of sucrose (~0.15 μCi/mL of radiolabeled) as an internal standard paracellular marker. The permeability of sucrose for each well was determined along with that of the compound of interest to ascertain the confluence of the monolayers. Transport rates for both the monolayers and the filters were then determined by taking samples at discrete time intervals and plotting the cumulative amount permeated as a function of time. Samples were analyzed by HPLC (Hewlett Packard, HP 1090) or counted on a liquid scintillation counter (Packard, Tri-Carb, A2700). Monolayers were deemed to be confluent and acceptable for permeability measurements when sucrose leakage was less than 15% per hour.

Permeability coefficients were then determined according to equation 1:

$$P = J/AC_o \qquad (1)$$

where J was the rate of appearance of the drug in the receiver chamber, $C_o$ was the initial concentration of the drug in the donor chamber, and A was the surface area of the filter. The in vitro BBB permeability was reported as the permeability coefficient of drugs across the monolayers, $P_m$, and was determined according to equation 2:

$$1/P_m = 1/P_e - 1/P_f \qquad (2)$$

where $P_e$ was the effective permeability coefficient across the monolayer and the filter and $P_f$ was the permeability coefficient across the filter only. Permeability measurements were done in at least triplicates for each compound.

EXAMPLE 4

Permeability Measurements

Transmembrane permeability of TBMEC,P11 monolayers was quantitated by sucrose, a non-metabolizable, membrane impermeant marker. The permeability coefficients of 0.1M sucrose solutions in HBSS for TBMEC,P11 monolayers compared to BMEC monolayers are presented in Table 1.

TABLE 1

| | $P \times 10^5$ (cm/sec) | |
|---|---|---|
| Compound | TBMEC-11 | BMEC |
| Sucrose | 2.6 ± 0.6 | 3.3 ± 0.6 |

Permeability of Select Compounds

The permeability coefficients of acyclovir and leucine at 0.1M in TBMEC,P11 and BMEC monolayers are shown in Table II. It can be seen that the permeability coefficients for these compounds in both transfected and primary cells are similar. These results demonstrate that the BMECs according to the present invention form monolayers substantially impermeable to low molecular weight molecules.

TABLE 2

| Compound | TBMEC-11 | BMEC |
|---|---|---|
| | P × 10$^5$ (cm/sec) | |
| Acyclovir | 5.2 ± 0.6 | 3.9 ± 1.0 |
| Leucine | 6.1 ± 2.2 | 4.3 ± 3.9 |

EXAMPLE 5

Construction of Plasmid pyMT

Construction of a modified polyoma virus early region encoding only the middle-T protein was made by the methods as described by Treisman, Novak, Favaloro and Kamen, Nature, Vol 292, Aug. 13, 1981, incorporated herein by reference.

In brief, a recombinant plasmid containing the full length viral (polyoma) wild type viral DNA was cut with the endonuclease Ava 1 to remove an intervening sequence that contained the middle-T antigen coding region. This fragment was ligated into a recombinant ampicillin-resistant vector, at sites previously cut with Msp 1 plus Ava 1 and dephosphorylated with calf alkaline phosphatase. The ligation product was transfected into E. coli strain HB101, and ampicillin-resistant colonies were selected. Small preparations of DNA was prepared from the resulting colonies and digested with AvaI, AvaII, Hinf1 and MspI and run on agarose-polyacrylamide gels to determine that the colonies contained the middle-T coding region fragment. A colony containing the appropriate digestion pattern by electrophoresis was termed pPyMT1 and propagated to produce milligram quantities of DNA by cesium chloride gradient purification, for transfection of mammalian cells. Studies from the reference cited above had determined that this recombinant plasmid containing the middle-T antigen could transform Fisher rat cells (F2408 cell line). Cells transfected with the pPyMT1 plasmid alone formed foci, grew poorly on plastic and grew poorly at low density.

REFERENCES

Audus, K. L., Bartel, R. L., Hidalgo, I. J., and Borchardt, R. T., The use of cultured epithelial and endothelial cells for drug transport and metabolism studies, Pharm. Res. 7, 435–451 (1990)

Masereeuw, R.; Jaehde, U.; Langemeijer, M. W. E.; de Boer, A. G.; Breimer, D. D. In vitro and in vivo transport of zidovudine (AZT) across the blood-brain barrier and the effect of transport inhibitors. Pharm. Res. 1994, 11, 324–330.

Méresse, S., Dehouck, M-P., Delorme, P., Bensaid, M., Tauber, J-P., Delbart, C., Fruchart, J-C., and Ceccelli, R., Bovine brain endothelial cells express tight junctions and monoamine oxidase activity in long-term culture, J. Neuorchem. 53, 1363–1371 (1989)

Pardridge, W. M., Triguero, D., Yang, J., and Cancilla, P. A., Comparison of in vitro and in vivo models of drug transcytosis through the blood-brain barrier, J. Pharmacol. Exp. Thera. 253, 884–891 (1990)

Cserr, H. F. and Bindgaard, M., Blood-brain interfaces in vertebrates: a comparative approach, Am. J. Physiol. 246, R277–R288 (1984)

Juillerat-Jeanneret, L., Aguzzi, A, Wiestler, O. D., Darekar, P., ands Jnazer, R. C., Dexamethasone selectively regulates the activity of enzymatic markers of cerebral endothelial cells lines, In Vitro Cell Dev. Biol. 28A, 537–543 (1992)

Soeda E., Arrand, J. R., Smolar, N., Walsh, J. E., and Griffin, B. E., Coding potential and regulatory signals of the polyoma virus genome, Nature, 283, 445–453 (1980)

Durieu-Tautmann, O., Foignant-Chaverot, N., Perdomo, J., Gounon, P., Strosberg, A. D., and Conrad, P. O., Immortalization of brain capillary endothelial cells with maintenance of structural characteristics of the blood-brain barrier endothelium, In vitro Cell. Dev. Bio. 27A, 771–778 (1991)

Seelig, A., A general pattern for substrate recognition by P-glycoprotein, Eur. J. Bioch. 251, 252–261 (1998)

Treisman, R., Novak, U., Favaloro, J. & Kamen, R. Transformation of rat cells by an altered polyoma virus genome expressing only the middle-T protein. Nature, 292, 595–600 (1981).

Bowman, P. D., Ennis, S. R., Rarey, K. E. Betz, A. L., and Goldstein, G. W., Brain microvessel endothelial cells in tissue culture: A model for study of blood-brain barrier permeability, Ann. Neurol. 14, 396–402 (1983)

Audus, K. L. and Borchardt, R. T., Characterization of an in vitro blood-brain barrier model system for studying drug transport and metabolism, Pharm, Res. 3, 81–87 (1986)

Brightman, M. W. and Neuwelt, E. A., (ed.), Implications of the blood-brain barrier and its manipulation, Vol. 1, Plenum Medical, New York, pp. 53–83 (1989).

What is claimed is:

1. A brain microvessel endothelial cell (BMEC) comprising a nucleic acid sequence encoding Middle-T antigen gene from a papovirus, wherein said cell is capable of forming monolayers substantially impermeable to low molecular weight molecules.

2. The brain microvessel endothelial cell according claim 1 wherein the papovirus is polyoma.

3. The brain microvessel endothelial cell according claim 1 wherein the low molecular weight molecule is a hydrophilic and/or lipophilic pharmaceutical.

4. The brain microvessel endothelial cell according claim 2 wherein the low molecular weight molecule is a hydrophilic and/or lipophilic pharmaceutical.

5. A method of measuring blood brain barrier permeability of a substance, wherein the permeability measured is passive diffusion or active transport, said method comprising:

provide BMECs according to claim 1 in one or more confluent monolayers;

contacting said substance with said confluent monolayer(s); and measuring the amount of said substance permeated across the BMEC monolayer(s).

6. The method of measuring blood brain barrier permeability of a substance according to claim 5 wherein said substance is a low molecular weight hydrophilic or lipophilic pharmaceutical.

7. The brain microvessel endothelial cell according claim 1 wherein the cell is TBMEC,P11 having the A.T.C.C. designation number CRL-12414.

* * * * *

```
                        SEQUENCE LISTING

<160> NUMBER OF SEQ ID NOS: 2

<210> SEQ ID NO 1
<211> LENGTH: 5297
<212> TYPE: DNA
<213> ORGANISM: Polyomavirus sp.
<220> FEATURE:
<221> NAME/KEY: gene
<222> LOCATION: (1)..(5297)
<223> OTHER INFORMATION: Polyoma T-antigen

<400> SEQUENCE: 1
gggggcccct ggcctccgct tactctggag aaaaagaaga gaggcattgt agaggcttcc      60
agaggcaact tgtcaaaaca ggactggcgc cttggaggcg ctgtggggcc acccaaattg     120
```

-continued

```
atataattaa gccccaaccg cctcttcccg cctcatttca gcctcaccac catcatggat      180
agagttctga gcagagctga caaagaaagg ctgctagaac ttctaaaact tcccagacaa      240
ctatgggggg attttggaag aatgcagcag gcatataagc agcagtcact gctactgcac      300
ccagacaaag gtggaagcca tgccttaatg caggaattga acagtctctg gggaacattt      360
aaaactgaag tatacaatct gagaatgaat ctaggaggaa ccggcttcca ggtaagaagg      420
ctacatgcgg atgggtggaa tctaagtacc aaagacacct ttggtgatag atactaccag      480
cggttctgca gaatgcctct tacctgccta gtaaatgtta aatacagctc atgtagttgt      540
atattatgcc tgcttagaaa gcaacataga gagctcaaag acaaatgtga tgccaggtgc      600
ctagtacttg gagaatgttt ttgtcttgaa tgttacatgc aatggtttgg aacaccaacc      660
cgagatgtgc tgaacctgta tgcagacttc attgcaagca tgcctataga ctggctggac      720
ctggatgtgc acagcgtgta taatccaagt aagtatcaag agggcgggtg ggtatttacg      780
gcctatattc ttacagggct ctcccctag aacggcggag cgaggaactg aggagagcgg       840
ccacagtcca ctacacgatg actactggtc attcagctat ggaagcaagt acttcacaag      900
ggaatggaat gatttcttca gaaagtggga ccccagctac cagtcgccgc ctaagactgc      960
cgagtcttct gagcaacccg acctattctg ttatgaggag ccactcctat cccccaaccc     1020
gagttctcca acagatacac ccgcacatac tgctggaaga agacgaaatc cttgtgttgc     1080
tgagcccgat gacagcatat ccccggaccc ccccagaact cctgtatcca gaaagcgacc     1140
aagaccagct ggagccactg gaggaggagg aggaggagta catgccaatg gaggatctgt     1200
atttggacat cctaccgggg gaacaagtac cccagctcat ccccccccct atcattccca     1260
gggcgggtct gagtccatgg gagggtctga ttcttcggga tttgcagagg gctcatttcg     1320
atccgatcct agatgcgagt cagagaatga gagctactca cagagctgct ctcagagctc     1380
attcaatgca acgccaccta agaaggctag ggaggaccct gctcctagtg actttcctag     1440
cagccttact gggtatttgt ctcatgctat ttattctaat aaaacgttcc cggcatttct     1500
agtatactcc accaaagaga aatgcaaaca attatatgat accataggga agttcaggcc     1560
cgaattcaaa tgcctggtcc attatgagga ggggggcatg ctgttctttc taactatgac     1620
taagcacagg gtttcagcag ttaagaatta ttgctctaag ctttgccgca gcttcctaat     1680
gtgtaaggca gtcaccaagc ctatggaatg ctatcaagtt gtaaccgcag caccatttca     1740
gttaataaca gaaaataagc caggcctcca ccaattcgag tttacagacg agccagaaga     1800
acagaaagca gtagactgga ttatggtagc agactttgca ctagaaaaca accttgatga     1860 tccctgtta attatggggt attatcttga ttttgccaaa gaggttcctt catgcataaa      1920
gtgtagcaaa gaggaaaccc gcctccaaat acattggaaa aaccatagaa agcatgcaga     1980
gaatgcagac ctcttcctga attgtaaagc tcaaaagaca atctgtcagc aggcagctgc     2040
gagtctggca tccaggagac tgaaattagt agagtgtacc cgcagccagc tattaaagga     2100
gagattgcaa cagtctctcc tcaggctaaa agaacttggc tcctccgatg ctctactcta     2160
cctagcaggt gtcgcttggt accagtgtct tttagaggac tttcctcaaa ccctgtttaa     2220
gatgcttaag ctgctaacag aaaatgtgcc aaaacgacgc aacatacttt ttagaggacc     2280
agttaattca ggaaagacag gcctagcagc cgcgcttatt agcctgttag gaggcaagtc     2340
tctcaacata aattgccctg cagataaact tgcttttgag cttggtgtgg cacaggacca     2400
gtttgtggtc tgttttgaag atgtaaaggg tcaaatagcc ttgaacaaac aactgcagcc     2460
```

-continued

```
agggatggga gtggctaatc tagataatct caggactacc tggaatggga gtgtaaaggt    2520
caatctagaa aaaagcaca gcaacaaaag gtcacaactc tttccaccct gtgtgtgtac    2580
aatgaatgaa tatctcctac cacaaacagt atgggcccgg tttcacatgg tgttggattt    2640
cacctgcaaa ccccatctgg cccaatctct tgaaaagtgt gaattttgc aaagggaaag    2700 aattattcag agtggagata cccttgccct attactcata tggaatttca cttcagatgt    2760
atttgatcct gatattcagg gtcttgtgaa ggaggttcgt gaccagtttg ctagtgagtg    2820
ctcctacagt ttgttttgtg atatactttg taatgtgcaa gaaggcgacg acccccttgaa    2880 ggacatatgt gatatagctg aatacacagt ttattgaata acattaatt tccaggaaat    2940 acagtctttg ttttttccaaa gcggtcaaca tagcgcgtca tatcagggtc cccggtaca    3000 ggttcagtcc catcatacac tctaacctcc tctacctggg tgttctcccc ttccatgggt    3060
tggccctgca cttgggggag catgttgttg aaaagggaac ttatgaggga ggccatggga    3120
tagggatttt tgacccatct ttttctcagg gtgattttga aatatctggg aaagcccttc    3180
tccagtgatg acacatagtt tcttgtaact ctccagccca ttatatctac acaggagagg    3240
tataggccct ctcctttaca gaggggccca actccatttt catctaggag cacagttgtc    3300
agggtgtttg tgaactgcag gacgggtgga gctgttgtgc ctccagtgta attgccaaag    3360
taccttgtgt tctcatttttt tgctggatct ggatgccaga tttcaactgg atacattccg    3420
tccttatcca gcttggcctt gctaattgga ttcaggactt ggtctttgtt gaccatgtcc    3480
ttctttgtga ttgttttgat tgttactacc ccttcttcct tgtattttgt tctggcatct    3540
gtcacaagtc cctggaggtc aagcggttcc ccgccaccag caaacacatg atattggctg    3600
ccttccactg gagtggaatt tcctttgtgt ttactgaatc tgtgggtttt gttgaaccca    3660
tgcacatcta acagtgagcc agagcccacc acctcggttt tcactgagac tgcctcccac    3720
atttgtaggg tgtcacaggt gaggtcctca ttgaggcatg ggaagctgga ctttgccata    3780
ctccatgtgg gaagtgtatt atttcgggga atccacgtat ctgatgtagc caaattaatc    3840
cctctgctcc aaccatagta ttgccctccc tctgttaggc tttcagggt gggtggctgc    3900 cccattctgg ggttcagaaa agcttctatt tctgtcacac tgtctggccc tgtcacaagg    3960
tccagcacct ccatacccc tttaataagc agtttgggaa cgggtgcggg tcttggacag    4020
gcctttgtac attttgtctc gcatttagag acgccgcttt ttcttttggg ggccatcttc    4080
ctctatgact gttgcccaag taggtgtgat atcaccgtac agccctagaa ttaaaggaag    4140
catccagtca ggagtgactc tttggtggga caccacctgg gcctgataga actttatcac    4200
ctcacctgac tcatcctgta tatgtgctgc aggggtaggc ccaccatttc ccatgctccc    4260
ttctatgcga ttaaagagtg ctctcctctg tggtggatta agacctagtt gcctataata    4320
gtcacttagt gatgagtacc ctgagctcgc tgatgaggca cctctgttga ttgcatctat    4380
ggctgactga ggagcattag aaaccaccca ccgggtgttt tcaagtagcc tagctaggcc    4440
atccaggaat gtatgtgtct gtcttacagt tagttctctt acagctcctt ccagtctgtg    4500
ttgtgtttcc tgcacaacca tttgccacac atatcttccc acggaatgaa gtaggccatg    4560
gccccaatca tgtactacat ttagagcatg agcaaactga ttaactcctg ggaagtatat    4620
atcgagaagg gctggatccc gccatggtat caacgccata tttctattta cagtagggac    4680
ctcttcgttt tgtaggtacc gctgtattcc tagggaaata gtagaggcac cttgaactgt    4740
ctgcatcagc catatagccc ccgctgttcg acttacaaac acaggcacag tactgacaaa    4800
cccatacacc tcctctgaaa tacccatagt tgctagggct gtctccgaac tcattacacc    4860
```

-continued

```
ctccaaagtc agagctgtaa tttcgccatc aagggcagcg agggcttctc cagataaaat    4920
agcttctgcc gagagtcccg taagggtaga cacttcagct aatccctcga tgaggtctac    4980
tagaatagtc agtgcggctc ccattttgaa aattcactta cttgatcagc ttcagaagat    5040
ggcggagggc ctccaacaca gtaattttcc tcccgactct taaaatagaa aatgtcaagt    5100
cagttaagca ggaagtgact aactgaccgc agctggccgt gcgacatcct cttttaatta    5160
gttgctaggc aactgccctc cagagggcag tgtggttttg caagaggaag caaaaagcct    5220
ctccacccag gcctagaatg tttccaccca atcattacta tgacaacagc tgttttttt     5280 agtattaagc agaggcc                                                    5297

<210> SEQ ID NO 2
<211> LENGTH: 1328
<212> TYPE: DNA
<213> ORGANISM: Polyomavirus sp.
<220> FEATURE:
<223> OTHER INFORMATION: middle T antigen polyoma virus from nt 73 -
      1500

<400> SEQUENCE: 2
tcatggatag agttctgagc agagctgaca agaaaaggct gctagaactt ctaaaacttc      60
ccagacaact atggggggat tttggaagaa tgcagcaggc atataagcag cagtcactgc     120
tactgcaccc agacaaaggt ggaagccatg ccttaatgca ggaattgaac agtctctggg     180
gaacatttaa aactgaagta tacaatctga aatgaatct aggaggaacc ggcttccagg      240
taagaaggct acatgcggat gggtggaatc taagtaccaa agacaccttt ggtgatagat     300
actaccagcg gttctgcaga atgcctctta cctgcctagt aaatgttaaa tacagctcat     360
gtagttgtat attatgcctg cttagaaagc aacatagaga gctcaaagac aaatgtgatg     420
ccaggtgcct agtacttgga gaatgttttt gtcttgaatg ttacatgcaa tggtttggaa     480
caccaacccg agatgtgctg aacctgtatg cagacttcat tgcaagcatg cctatagact     540
ggctggacct ggatgtgcac agcgtgtata atccaagtaa gtatcaagag ggcgggtggg     600
tatttacggc ctatattctt acagggctct cccctagaa cggcggagcg aggaactgag      660
gagagcggcc acagtccact acacgatgac tactggtcat tcagctatgg aagcaagtac     720
ttcacaaggg aatggaatga tttcttcaga aagtgggacc ccagctacca gtcgccgcct     780
aagactgccg agtcttctga gcaacccgac ctattctgtt atgaggagcc actcctatcc     840
cccaacccga gttctccaac agatacaccc gcacatactg ctggaagaag acgaaatcct     900
tgtgttgctg agcccgatga cagcatatcc ccggaccccc ccagaactcc tgtatccaga     960
aagcgaccaa gaccagctgg agccactgga ggaggaggag gaggagtaca tgccaatgga    1020
ggatctgtat ttggacatcc taccggggga caagtaccc cagctcatcc ccccccctat     1080
cattcccagg gcgggtctga gtccatggga gggtctgatt cttcgggatt tgcagagggc    1140
tcatttcgat ccgatcctag atgcgagtca gagaatgaga gctactcaca gagctgctct    1200
cagagctcat tcaatgcaac gccacctaag aaggctaggg aggaccctgc tcctagtgac    1260
tttcctagca gccttactgg gtatttgtct catgctattt attctaataa aacgttcccg    1320
gcatttct                                                            1328
```